United States Patent
Park et al.

(10) Patent No.: US 10,870,098 B2
(45) Date of Patent: Dec. 22, 2020

(54) METHOD OF INHIBITING REACTOR FOULING AND OLIGOMERISATION OF OLEFIN USING THE SAME

(71) Applicants: SK Innovation Co., Ltd., Seoul (KR); SK Global Chemical Co., Ltd., Seoul (KR)

(72) Inventors: Hyo Seung Park, Daejeon (KR); Woo Sung Jung, Daejeon (KR); In Hyoup Song, Daejeon (KR); Il Gu Jung, Daejeon (KR); Jong Ho Choi, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 34 days.

(21) Appl. No.: 16/305,222

(22) PCT Filed: Jan. 8, 2018

(86) PCT No.: PCT/KR2018/000338
§ 371 (c)(1),
(2) Date: Nov. 28, 2018

(87) PCT Pub. No.: WO2018/174390
PCT Pub. Date: Sep. 27, 2018

(65) Prior Publication Data
US 2019/0308158 A1    Oct. 10, 2019

(30) Foreign Application Priority Data
Mar. 23, 2017    (KR) .................. 10-2017-0037037

(51) Int. Cl.
*B01J 19/00*    (2006.01)
*C07C 2/36*    (2006.01)
(Continued)

(52) U.S. Cl.
CPC ............. *B01J 19/002* (2013.01); *B01J 31/06* (2013.01); *B01J 31/143* (2013.01); *B01J 31/146* (2013.01);
(Continued)

(58) Field of Classification Search
None
See application file for complete search history.

(56) References Cited

U.S. PATENT DOCUMENTS 3,984,387 A    10/1976    Liu et al.
4,012,574 A    3/1977    Jones et al.
(Continued)

FOREIGN PATENT DOCUMENTS

JP    2010526647 A    8/2010
JP    5458322 B2    4/2014
(Continued)

OTHER PUBLICATIONS

Opalindia, Material Safety Data Sheet High Density Polyethylene (HDPE), opalindia, Jan. 3, 2016, pp. 1-6. (Year: 2016).*
(Continued)

*Primary Examiner* — Philip Y Louie
(74) *Attorney, Agent, or Firm* — The Webb Law Firm

(57) ABSTRACT

Provided are a fouling inhibitor and a method of oligomerizing an olefin using the same. More particularly, in the method of oligomerizing an olefin, it is possible to minimize a total amount of polymers produced during a reaction and basically inhibit fouling of the polymers produced during the reaction onto an inner wall of a reactor by injecting a predetermined fouling inhibitor.

11 Claims, 1 Drawing Sheet

(51) Int. Cl.
*B01J 31/14* (2006.01)
*B01J 31/24* (2006.01)
*C08L 91/06* (2006.01)
*B01J 31/06* (2006.01)
*C08L 91/08* (2006.01)
*C07C 11/04* (2006.01)
*C07C 11/107* (2006.01)

(52) U.S. Cl.
CPC ............ *B01J 31/2409* (2013.01); *C07C 2/36* (2013.01); *C08L 91/06* (2013.01); *C08L 91/08* (2013.01); *B01J 2219/00247* (2013.01); *B01J 2231/20* (2013.01); *B01J 2231/30* (2013.01); *B01J 2531/62* (2013.01); *C07C 11/04* (2013.01); *C07C 11/107* (2013.01); *C07C 2523/26* (2013.01); *C07C 2531/14* (2013.01); *C07C 2531/24* (2013.01)

(56) References Cited

U.S. PATENT DOCUMENTS

| | | |
|---|---|---|
| 4,956,427 A | 9/1990 | Jenkins, III et al. |
| 5,677,375 A | 10/1997 | Rifi et al. |
| 6,080,903 A * | 6/2000 | Stine .................. C07C 2/08 585/326 |
| 6,380,451 B1 | 4/2002 | Kreischer et al. |
| 8,227,653 B2 | 7/2012 | Weber et al. |
| 8,609,924 B2 | 12/2013 | Han et al. |
| 9,487,456 B2 | 11/2016 | Overett et al. |
| 2005/0113622 A1* | 5/2005 | Drent ................ B01J 31/143 585/521 |
| 2007/0270558 A1 | 11/2007 | Scherrer et al. |
| 2010/0167058 A1 | 7/2010 | Van Egmond et al. |
| 2012/0016097 A1 | 1/2012 | Weber et al. |
| 2013/0303817 A1 | 11/2013 | Shaik et al. |
| 2016/0010006 A1 | 1/2016 | Subbiah et al. |

FOREIGN PATENT DOCUMENTS

| | | |
|---|---|---|
| KR | 100271582 B1 | 11/2000 |
| KR | 1020100097284 A | 9/2010 |
| KR | 101145090 B1 | 5/2012 |
| WO | 0147838 A1 | 7/2001 |

OTHER PUBLICATIONS

PubChem, National Center for Biotechnology Information. PubChem Database. Eicosane, CID=8222, https://pubchem.ncbi.nlm.nih.gov/compound/Eicosane, accessed on Feb. 26, 2020, 1 page (Year: 2020).*

Marcus Oil and Chemical, Marcus Homopolymer Polyethylene Waxes—Product Data Sheet, 2000, 1 page. (Year: 2000).*

* cited by examiner

[Fig. 1]
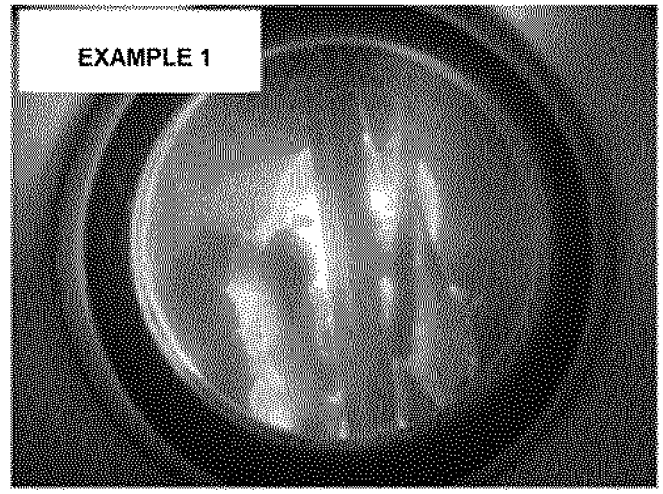
[Fig. 2]
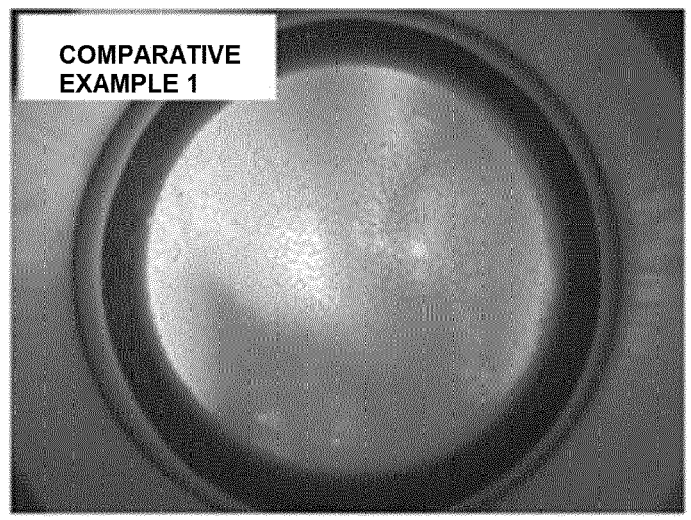
[Fig. 3]
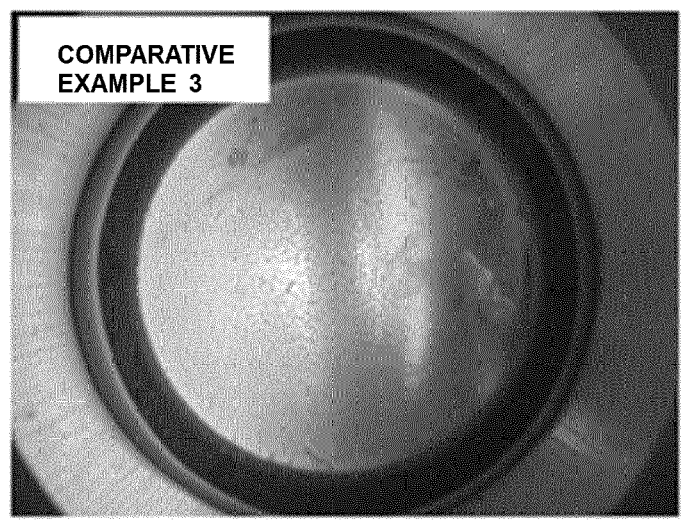

US 10,870,098 B2

METHOD OF INHIBITING REACTOR FOULING AND OLIGOMERISATION OF OLEFIN USING THE SAME

CROSS-REFERENCE TO RELATED APPLICATIONS

This application is the United States national phase of International Application No. PCT/KR2018/000338 filed Jan. 8, 2018, and claims priority to Korean Patent Application No. 10-2017-0037037 filed Mar. 23, 2017, the disclosures of which are hereby incorporated in their entirety by reference.

TECHNICAL FIELD

The present invention relates to a method of inhibiting reactor fouling and a method of oligomerizing an olefin using the same, and more particularly, to an oligomerisation olefin capable of effectively reducing fouling by injecting a predetermined fouling inhibitor.

BACKGROUND ART

A linear alpha-olefin (LAO) required to prepare a high-value linear low-density polyethylene is obtained by an oligomerization reaction of an olefin. However, in the oligomerization reaction of an olefin, a significant amount of butane, other olefins, isomers thereof, a specific higher oligomer, a polymer (for example, polyethylene), and the like, are produced together, and a catalyst separated from a carrier and some of by-products (for example, polyethylene) produced at the time of the oligomerization reaction of the olefin are attached to an inner wall of a reactor or a surface of a heat exchanger installed in the reactor or float in the reactor to thereby form fouling.

The fouling in the reactor as described above makes it difficult to control a reaction heat and inhibits uniform diffusion of an olefin monomer, thereby deteriorating heat efficiency and production efficiency.

Therefore, various technologies for suppressing the fouling in the reactor as described above have been suggested. First, a method of hydrolyzing, hardening, and coating amino silicone on a metal surface in a reactor was disclosed in U.S. Pat. No. 4,956,427. However, this method has a problem in that at the time of performing a coating operation, production needs to be stopped for a long period of time, such that a high cost is required. Next, a method of injecting an inert gas such as nitrogen, helium, or the like, into a reactor together with an olefin monomer was suggested in U.S. Pat. No. 3,984,387, but has a problem in that a polymerization activity is decreased due to a decrease in a partial pressure of the olefin monomer. Next, a method of injecting a fouling inhibitor including a perfluorocarbon group and a hydrophilic group at the time of polymerization was suggested in U.S. Pat. No. 4,012,574, but has a problem in that an effect of inhibiting the fouling is not sufficient.

Therefore, the present inventors confirmed that it is possible to improve workability and productivity by effectively overcoming problems in a process such as fouling, plugging, and the like, in a reactor in the method of oligomerizing an oligomer, thereby completing the present invention.

RELATED ART DOCUMENT

Patent Document

U.S. Pat. No. 4,956,427
U.S. Pat. No. 3,984,387
U.S. Pat. No. 4,012,574

DISCLOSURE OF INVENTION

Technical Problem

An object of the present invention is to provide a predetermined hydrocarbon based compound useful as a fouling inhibitor.

Another object of the present invention is to provide a method of inhibiting fouling capable of significantly decreasing the fouling generated in a reaction without a negative influence on reaction efficiency by using a predetermined hydrocarbon based compound.

Another object of the present invention is to provide a method of oligomerizing an olefin capable of significantly decreasing fouling by suppressing by-products (for example, polyethylene) from being produced while effectively suppressing the produced by-products from being adhered in a reactor at the time of performing an oligomerization reaction of the olefin.

Particularly, in the method of oligomerizing an olefin according to the present invention, it may be easy to remove reaction heat due to the above-mentioned effects, a catalytic activity may be maximized, and 1-hexene and 1-octene may be highly selectively prepared by the oligomerization reaction.

Another object of the present invention is to provide an alpha-olefin oligomer composition containing a predetermined hydrocarbon based compound according to the present invention as a fouling inhibitor.

Solution to Problem

In one general aspect, there is provided a linear or branched hydrocarbon based compound having a melting point of 150° C. or less as a fouling inhibitor. The hydrocarbon based compound may be a natural or synthetic hydrocarbon based compound, and preferably have an average carbon number of 15 or more in each molecule.

In another general aspect, there is provided a method of inhibiting fouling by using a predetermined fouling inhibitor. The method of inhibiting fouling may significantly overcome problems in a process such as fouling, plugging, and the like, in a reactor by using the predetermined fouling inhibitor. Here, the method may be applied to a solution reaction, a slurry reaction, a vapor phase reaction, and the like, without limitations.

According to an exemplary embodiment of the present invention, an effect of decreasing fouling may be significantly improved, thereby making it possible to trimerize and/or tetramerize an olefin, particularly, ethylene with a high activity to produce 1-hexene and 1-octene with a high selectivity.

In detail, the method of oligomerizing an olefin according to the exemplary embodiment of the present invention may include: injecting a petroleum based wax or polyolefin wax having a melting point of 30 to 130° C., a cocatalyst, and a main catalyst into a medium injected into a reactor; and injecting the olefin into the reactor to perform a reaction.

According to the exemplary embodiment of the present invention, even in the case of adding a small amount of a fouling inhibitor at the time of oligomerization of the olefin, fouling generated in the reactor may be significantly decreased by minimizing a production amount of by-products produced during the reaction, such that workability and productivity may be improved.

Advantageous Effects of Invention

According to the present invention, it is possible to basically prevent polymers produced during a reaction from fouling on an inner surface of a reactor by minimizing a total amount of by-products (for example, polyethylene) produced during the reaction, that is, an adherent polymer and a floating polymer. Therefore, heat conduction in the inner wall of the reactor may be constantly maintained, such that it may be easy to control a temperature at the time of performing a reaction, and a catalytic activity may be maximized.

According to the present invention, since the catalytic activity is improved due to an effectively controlled effect of decreasing fouling, the oligomerization reaction of the olefin may be rapidly initiated, and stable operation and excellent reproducibility may be implemented.

Further, according to the present invention, technical obstacles in decreasing a production amount of the by-products produced during the reaction in technologies in the related art may be overcome, and an unexpected synergic effect on decreasing the production amount of the by-products produced during the reaction may be achieved, thereby making it possible to obtain an effect of increasing production efficiency.

BRIEF DESCRIPTION OF DRAWINGS

The above and other objects, features and advantages of the present invention will become apparent from the following description of preferred embodiments given in conjunction with the accompanying drawings, in which:

FIG. 1 is an image obtained by photographing an inner portion of a reactor after a reaction in Example 1 according to the present invention.

FIG. 2 is an image obtained by photographing an inner portion of a reactor after a reaction in Comparative Example 1 according to the present invention.

FIG. 3 is an image obtained by photographing an inner portion of a reactor after a reaction in Comparative Example 3 according to the present invention.

BEST MODE FOR CARRYING OUT THE INVENTION

Hereinafter, a fouling inhibitor according to the present invention and a method of oligomerizing an olefin capable of effectively decreasing fouling using the fouling inhibitor will be described in detail. Here, technical terms and scientific terms used in the present specification have the general meaning understood by those skilled in the art to which the present invention pertains unless otherwise defined, and a description for the known function and configuration obscuring the present invention will be omitted in the following description.

As used herein, the term "fouling" means a problem in a continuous work caused by by-products produced during a reaction discontinuously generated in a reactor at the time of oligomerizing the olefin, and the fouling is present in at least two different types. The two types of fouling are referred to as an adherent polymer or a floating polymer depending on a position at which the by-products produced during the reaction are produced in the reactor.

As used herein, the term "oligomerization" means a chemical process that links monomeric compounds to form dimers, trimers, tetramers, or longer chain molecules (oligomers). Depending on the number of olefins to be polymerized, the oligomerization is referred to as "trimerization" and "tetramerization", which are collectively referred to as "multimerization".

As used herein, the term "hydrocarbon based compound", which is a linear or branched hydrocarbon compound, may have an average carbon number of 15 or more in each molecule. Further, the hydrocarbon based compound may be a purified single compound or a blend of two or more compounds having different average carbon number in each molecule from each other.

As used herein, the term "petroleum based wax", which may mean a soft, oily or semi-solid mixture obtained from high boiling point hydrocarbons (for example, petroleum) and hydrocarbons which are generally liquids at room temperature (20° C.), means a semi-solid mixture in the present invention.

As used herein, the term "paraffin wax", which is one of the petroleum based waxes, has a linear hydrocarbon at a ratio of 60 wt % or more based on a total weight thereof. As an example, the paraffin wax may have an average carbon number of 18 to 45 in each molecule.

As used herein, the term "microcrystalline wax", which is one of the petroleum based waxes, has a branched hydrocarbon (for example, isoparaffin, or the like) at a ratio higher than that of the paraffin wax, and may also further include a cyclic hydrocarbon.

As used herein, the term "petroleum jelly", which is one of the petroleum based waxes, may be obtained by adjusting a viscosity of the microcrystalline wax to a desired viscosity using white mineral oil. As a commercialized example of petroleum jelly, petroleum jelly referred to as "Vaseline® (trade name)" may be obtained. A melting point of the commercial "Vaseline®" is about 48 to 85° C., and the petroleum jelly may be implemented so as to have various physical properties by blending a single oil selected from mineral oil, aromatic oil, naphthene based oil, paraffin based oil, and the like; triglyceride-based vegetable oil such as castor oil, an the like, synthetic hydrocarbon oil such as polybutene oil, and the like, silicon oil, and the like, or an arbitrary combination thereof while adjusting a content of the oil. Further, as used herein, the term "melting point (Tm)" means a temperature at a point corresponding to a maximum endothermic peak temperature, and the melting point was measured according to ASTM D2117.

A fouling inhibitor according to an exemplary embodiment of the present invention may have an excellent effect of decreasing fouling and be applied to solution polymerization, slurry polymerization, vapor phase polymerization, and the like, without limitations.

Further, the fouling inhibitor according to the exemplary embodiment of the present invention does not have an influence on physical properties of a linear alpha olefin (for example, 1-hexene, 1-octene, or the like) produced by the above-mentioned oligomerization reaction, and even though a use amount is small, the fouling inhibitor has an excellent effect of decreasing fouling.

The fouling inhibitor according to the exemplary embodiment of the present invention may be a linear or branched hydrocarbon based compound having a melting point of 150° C. or less.

The hydrocarbon based compound may have an average carbon number of 15 or more in each molecule, in order to satisfy the above-mentioned melting point range. Preferably, the hydrocarbon based compound may be a low-molecular weight compound having an average carbon number of 15 to 50 in each molecule, and more preferably, an average carbon number of 15 to 30 in each molecule.

The low-molecular weight compound, which is one of the examples of the hydrocarbon based compound, may be preferably a semi-solid, and a molecular weight thereof may be 200 to 1,000. Here, the molecular weight of the low-molecular weight compound may be preferably 200 to 800, and more preferably 200 to 500.

In addition, the hydrocarbon based compound may be a high-molecular weight compound having an average carbon number more than 50 in each molecule, in order to satisfy the above-mentioned melting point range.

The high-molecular weight compound, which is one of the examples of the hydrocarbon based compound, may be a semi-solid or solid, and a weight average molecular weight thereof may be 10,000 or less. Here, the molecular weight of the high-molecular weight compound may be preferably 1,000 to 9,000, and more preferably 2,000 to 6,000.

Further, the fouling inhibitor according to the exemplary embodiment of the present invention may be a hydrocarbon based compound having a hetero atom ratio of 0.01 or less in each molecule, preferably, an average hetero atom ratio of 0.0001 to 0.01 in each molecule. Here, the hetero atom ratio may mean a ratio of the number of hetero atoms to the number of carbon atoms (the number of hetero atoms/the number of carbon atoms), wherein the hetero atom may be selected from B, N, O, S, P, Si, and the like, but is not limited thereto.

A specific example of the fouling inhibitor according to the exemplary embodiment of the present invention may be as follows in view of supply convenience and production cost while having a synergic effect on fouling inhibition efficiency during the reaction, but is not limited thereto.

A specific example of the fouling inhibitor according to the exemplary embodiment of the present invention may be one or more hydrocarbon based compounds selected from natural waxes and synthetic waxes having a melting point of 150° C. or less.

Examples of the natural wax may include petroleum based waxes including petroleum jelly, paraffin wax, microcrystalline wax, and the like; mineral based waxes including ozocerite (earth wax), sericin, and the like; and animal-vegetable-based waxes including candelilla wax, carnauba wax, japan wax, esparto grass wax, cork wax, guaruma wax, rice germ oil wax, sugar cane wax, ouricury wax, montan wax, beeswax, shellac wax, spermaceti, lanolin (wool wax), uropygial grease, and the like; etc., and a chemically modified wax form of the natural wax may also be included in the wax according to an aspect of the present invention. Here, in view of the above-mentioned effect desired in the present invention, the petroleum based wax may be preferred.

Examples of the synthetic wax may include hydroisomerised wax, hydroisomerised Fischer-Tropsch wax, polyolefin wax, Fischer-tropsch wax, and the like. Here, in view of the above-mentioned effect desired in the present invention, the polyolefin wax (for example polyethylene wax, polypropylene wax, and the like) may be preferred.

A specific example of the fouling inhibitor according to the exemplary embodiment of the present invention may be a hydrocarbon based compound having a melting point of 30 to 150° C.

Further, a specific example of the fouling inhibitor according to the exemplary embodiment of the present invention may be a petroleum based wax having a melting point of 30 to 130° C.

In addition, a specific example of the fouling inhibitor according to the exemplary embodiment of the present invention may be a polyolefin wax having a melting point of 30 to 130° C.

Hereinafter, a method of inhibiting fouling by using the fouling inhibitor according to the exemplary embodiment of the present invention will be described. The fouling inhibitor is used in an oligomerization process of an olefin.

A method of inhibiting fouling according to an exemplary embodiment of the present invention includes: injecting a linear or branched hydrocarbon based compound having a melting point of 150° C. or less and a carbon number of 15 or more.

Here, injection conditions of the hydrocarbon based compound in the method are not limited. For example, the hydrocarbon based compound may be injected prior to a cocatalyst and a main catalyst for oligomerization of the olefin. Alternatively, the hydrocarbon based compound may also be injected during injection of the cocatalyst and the main catalyst, or additionally injected after injection of the cocatalyst and the main catalyst is completed.

In the method of inhibiting fouling according to the exemplary embodiment of the present invention, a use amount of the hydrocarbon based compound is not limited. However, the hydrocarbon based compound may be used in a range of 0.05 to 10 wt % in a medium used in a reaction and suitably adjusted and used in a range of preferably 0.1 to 5 wt %, and more preferably 0.1 to 3 wt %.

According to the exemplary embodiment of the present invention, it is estimated that the hydrocarbon based compound may serve as a lubricant in the reaction to effectively suppress polymers produced during the reaction from being adhered onto an inner wall of a reactor, and change a formation behavior of polymers produced during the reaction as by-products to minimize a total amount of the polymers.

Therefore, heat conduction in the inner wall of the reactor may be constantly maintained, such that it may be easy to control a reaction heat, and the hydrocarbon based compound assists in uniform diffusion of the olefin and catalytic activity, thereby improving production efficiency.

More specifically, as the method of inhibiting fouling by using the fouling inhibitor according to the exemplary embodiment of the present invention, a method of oligomerizing an olefin will be described.

According to the exemplary embodiment of the present invention, at the time of oligomerizing the olefin, it is possible to basically prevent problems due to adhesion of polymers produced during the reaction on the inner wall of the reactor while minimizing a production amount of by-products, that is, high-molecular weight polyolefin.

Therefore, according to the exemplary embodiment of the present invention, at the time of oligomerizing the olefin, it is possible to overcome problems occurring in a process such as fouling, plugging, and the like, thereby providing improved workability and productivity. Further, a production amount of a high-molecular weight polyolefin may be effectively suppressed, thereby making it possible to prevent catalytic activity from being decreased during the reaction. Here, the polyolefin is adhered into the reactor to inhibit heat conduction, thereby serving to deteriorate a production yield of LAO, and induce the reactor so as not to perform the process for a long period of time.

Further, according to the exemplary embodiment of the present invention, due to improved catalytic activity, it is possible to trimerize and/or tetramerize, particularly ethylene to produce 1-hexene and 1-octene with a high selectivity.

A method of oligomerizing an olefin according to the exemplary embodiment of the present invention includes: injecting a fouling inhibitor containing a hydrocarbon based compound having a melting point of 30 to 130° C. into a reactor; injecting a catalyst composition into the reactor; and injecting the olefin into the reactor to perform an oligomerization reaction. The hydrocarbon based compound may be one or more selected from petroleum based wax and polyolefin wax.

Here, an injection sequence of the hydrocarbon based compound and the catalyst composition does not affect the reaction, and the injection sequence may be suitably adjusted depending on process convenience. Further, the catalyst composition may contain a main catalyst alone, or be a mixture in which a main catalyst and a cocatalyst are mixed with each other.

In the method of oligomerizing an olefin according to the exemplary embodiment of the present invention, the petroleum based wax may be one or more selected from petroleum jelly, paraffin wax, microcrystalline wax, and the like. In the present invention, as the petroleum based wax satisfying the melting point condition, the petroleum jelly is preferred in that the petroleum jelly is excellent in view of the desired effect, but the present invention is not limited thereto.

Further, in the method of oligomerizing an olefin according to the exemplary embodiment of the present invention, the polyolefin wax may be one or more selected from polyethylene wax, polypropylene wax, and the like. In the present invention, as the polyolefin wax satisfying the melting point condition, the polyethylene wax is preferred in that the polyethylene wax is excellent in view of the desired effect, but the present invention is not limited thereto.

In the case of using petroleum based wax and/or polyolefin wax satisfying predetermined physical properties according to the present invention, fouling in the reactor may be effectively suppressed and the catalytic activity may be significantly improved by decreasing a total amount of by-products produced during the reaction, and oligomerization of an olefin, particularly, trimerization and/or tetramerization of ethylene, may be performed with a high selectivity.

In the method of oligomerizing an olefin according to the exemplary embodiment of the present invention, a use amount of the petroleum based wax is not limited. However, the petroleum based wax may be used in a range of 0.05 to 10 wt % based on a total weight of a medium in an oligomerization process of the olefin, and suitably adjusted and used in a range of preferably 0.1 to 5 wt %, and more preferably 0.1 to 3 wt %.

In the method of oligomerizing an olefin according to the exemplary embodiment of the present invention, the main catalyst is not limited as long as it is a complex type catalyst capable of oligomerizing the olefin, but the main catalyst may be preferably a main catalyst including a transition metal and coordinated with a hetero atom ligand.

Preferably, the main catalyst according to the present invention may be a complex type catalyst in which the transition metal and a hetero atom ligand represented by the following Chemical Formula 1 are coordinated with each other.

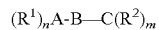   [Chemical Formula 1]

[In Chemical Formula 1]

A and C are each independently selected from the group consisting of phosphorus, arsenic, antimony, oxygen, bismuth, sulfur, selenium, and nitrogen, B is a linking group between A and C, n and m are each independently integers determined by valences and oxidation states of A and C, respectively, and $R^1$ and $R^2$ are each independently selected from the group consisting of substituted or unsubstituted hydrocarbyl and substituted or unsubstituted heterohydrocarbyl, $R^1$(s) are equal to or different from each other when n≥2, and $R^2$(s) are equal to or different from each other when m≥2.]

The hydrocarbyl or heterohydrocarbyl means a radical having one binding site induced from hydrocarbon or heterohydrocarbon, and a hydrocarbylene or heterohydrocarbylene means a radical having two binding sites induced from hydrocarbon or heterohydrocarbon, wherein the term "hetero" means that carbon is substituted with a hetero atom such as O, S, N, B, Si, P, or the like.

Further, the substitution may be each independently selected from the group consisting of hydrocarbyl, heterohydrocarbyl, halogen, and the like. As a non-restrictive example, the substitution may be selected from (C6-C20) aryl, (C6-C20)ar(C1-C10)alkyl, (C1-C10)alkyl, (C2-C10) alkenyl, (C2-C10)alkynyl, (C3-C7)cycloalkyl, hetero(C5-C20)aryl, hetero(C3-C7)cycloalkyl, (C1-C10)alkoxy, (C6-C20)aryloxy, —$NR^{21}R^{22}$, fluoro, chloro, bromo, iodo, and the like, wherein $R^{21}$ and $R^{22}$ are each independently further substituted with one or more substituents selected from (C1-C10)alkyl, (C1-C10)alkoxy, (C6-C20)aryloxy, halogen, and the like.

B of the ligand according to the exemplary embodiment of the present invention may be selected from an organic linking group including substituted or unsubstituted hydrocarbylene and substituted or unsubstituted heterohydrocarbylene; and an inorganic linking group including a single atom link A non-restrictive example thereof may be selected from an organic linking group such as methylene, dimethylmethylene, ethane-1,2-diyl, ethene-1,2-diyl, 1,2-propylene, propane-1,2-diyl, propane-1,3-diyl, cyclopropane-1,1-diyl, cyclopropane-1,2-diyl, butane-2,3-diyl, cyclobutane-1, 2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracene-diyl, 1,2-catecholate, 1,2-diarylhydrazine-1,2-diyl (—N(Ar)—N(Ar)—, here, Ar is aryl), 1,2-dialkylhydrazine-1,2-diyl (—N(Alk)-N(Alk)-, here, Alk is alkyl or cycloalkyl), 1-alkyl-2-arylhydrazine-1,2-diyl (—N(Alk)-N(Ar)—, here, Alk is alkyl or cycloalkyl, Ar is aryl), —N(R')—$X_1$—N(R")— (here, R' and R" are each independently alkyl, cycloalkyl, or aryl, $X_1$ is hydrocarbylene), =C(R')—N (R")—, =C(W—C(R")(R'")— (here, = is a double bond, R', R", and R'" are each independently hydrogen, alkyl, cycloalkyl, or aryl), —B(R')—, —Si(R')$_2$—, —P(R')—, and —N(R')— (here, R' is hydrogen, hydrocarbyl, heterohydrocarbyl, or halogen); and an inorganic linker group such as a single- or two-atom linker spacer.

The transition metal according to the exemplary embodiment of the present invention may be preferably chromium.

Chromium may be provided from one or more chromium precursor selected from chromium(III) acetylacetonate, chromium trichloride tristetrahydrofuran, chromium (III)2-ethylhexanoate, and the like, but is not limited thereto.

Further, the hetero atom ligand according to the exemplary embodiment of the present invention has a —P—C—C—P— backbone structure. In view that it is possible to change activities and selectivity of trimerization and tetramerization reactions so as to be suitable for an object depending on a stereoscopic change in structure in the vicinity of a carbon atom between two phosphine atoms, and it may be more easy to asymmetrically control a space, a preferable example of the hetero atom ligand may be a ligand represented by the following Chemical Formula 2, and carbon in the backbone structure has a chiral carbon having a pair of (R,R) or (S,S), but is not limited thereto.

[Chemical Formula 2]

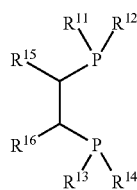

[In Chemical Formula 2, $R^{11}$ to $R^{14}$ are each independently selected from the group consisting of substituted or unsubstituted hydrocarbyl and substituted or unsubstituted heterohydrocarbyl; and $R^{15}$ and $R^{16}$ are each independently substituted or unsubstituted hydrocarbyl, or are linked with each other by substituted or unsubstituted hydrocarbylene or substituted or unsubstituted heterohydrocarbylene to form a ring.]

In the method of oligomerizing an olefin according to the exemplary embodiment of the present invention, the main catalyst may be a catalyst in which chromium provided from the chromium precursor and the ligand represented by Chemical Formula 2 are bonded to each other.

In the method of oligomerizing an olefin according to the exemplary embodiment of the present invention, the cocatalyst, which is injected in order to increase an activity of the main catalyst and more stably implement a catalytic activity, is not limited as long as it is a generally used compound. A non-restrictive example of the cocatalyst may include an organic aluminum compound, an organic boron compound, and the like.

Examples of the organic aluminum compound may include aluminoxane, an alkyl aluminum compound, an alkyl aluminum chloride compound, an alkyloxy aluminum compound, an aryloxy aluminum compound, and the like.

Here, the aluminoxane may be a linear, cyclic, or cage aluminoxane, or the like. A non-restrictive example of aluminoxane may include alkylaluminoxane selected from methylaluminoxane (MAO), methylisobutylaluminoxane (MMAO), ethylaluminoxane (EMAO), isobutylaluminoxane (IBAO), tetraisobutylaminoxane (TIBAO), and modified alkylaluminoxane (for example, $[(R^a)_n(R^b)_{1-n}AlO]_m$, where, $R^a$ and $R^b$ are each independently hydrocarbyl, halogen-substituted hydrocarbyl, or halogen, n is a number between 0 and 1, and m is an integer of 1 or more), such as modified methylaluminoxane (mMAO), and the like.

Further, non-restrictive examples of the alkyl aluminum compound may include trimethylaluminum, triethylaluminum, tripropylaluminum, triisobutylaluminum, diisobutylaluminum, trioctylaluminum, and the like, and non-restrictive examples of alkyl aluminum chloride compound may include dimethylaluminumchloride, diethylaluminumchloride, dipropylaluminum chloride, diisobutylaluminumchloride, dioctylaluminumchloride, methylaluminumdichloride, ethylaluminumdichloride, propylaluminumdichloride, isobutylaluminumdichloride, hexylaluminumdichloride, methylaluminum sesquichloride, ethylaluminum sesquichloride, and the like. Further, a non-restrictive example of the alkyloxy aluminum compound may include dimethylaluminum hydride, diethylaluminum hydride, dipropylaluminum hydride, diisopropylaluminum hydride, diisobutylaluminum hydride, dioctylaluminum hydride, and the like, and a non-restrictive example of the aryloxy aluminum compound may include triphenoxyaluminum, dimethylaluminum phenoxide, methylaluminum diphenoxide, and the like.

Further, a non-respective example of the organic boron compound may include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-tetrafluorophenyl)borate, tetrakis(2,2,4-trifluorophenyl)borate, phenylbis(pentafluorophenyl)borate, tetrakis(3,5-bistrifluoromethylphenyl)borate, and the like; ferrocenium tetrakis(pentafluorophenyl)borate, 1,1'-dimethylferrocenium tetrakis(pentafluorophenyl)borate, tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis (pentafluorophenyl)borate, tripropylammonium tetrakis (pentafluorophenyl)borate, tri(n-butyl)ammonium tetrakis (pentafluorophenyl)borate, tri(n-butyl)ammonium tetrakis (3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, tri(dimethylphenyl)phosphonium tetrakis(pentafluorophenyl)borate, and the like. Among them, it is preferable that the organic boron compound is selected from N,N-dimethylanilinium tetrakispentafluorophenylborate, triphenylmethylinium tetrakispentafluorophenylborate, and trispentafluoroborane, but is not limited thereto.

Here, the cocatalyst may be contained so that a molar ratio of an aluminum or boron atom to a chromium atom of the main catalyst is 1:0.01 to 1:1000, preferably, 1:0.1 to 1:500, and more preferably 1:01 to 1:100, respectively.

In the method of oligomerizing an olefin according to the exemplary embodiment of the present invention, the cocatalyst may be dissolved or uniformly dispersed in a reaction solvent (medium), and a preferable example of the reaction solvent may include (C3-C20) hydrocarbon based solvent. Here, a non-restrictive example of the hydrocarbon based solvent may be one or more selected from butane, pentane, hexane, heptane, octane, isooctane, nonane, decane, dodecane, cyclohexane, methylcyclohexane (MCH), methylcyclopentane (MCP), benzene, toluene, xylene, ethylbenzene, and the like, and preferably one or more selected from cyclohexane, methylcyclohexane (MCH), methylcyclopentane (MCP), and the like, but is not limited thereto.

In the method of oligomerizing an olefin according to the exemplary embodiment of the present invention, as an example of an oligomer to be produced, 1-butene, 1-hexene, 1-octene, 1-decene, 1-dodecene, 1-tetradecene, 1-octadecene, or the like, may be prepared. In the present invention, particularly, 1-hexene and/or 1-octene may be prepared with a high selectivity, such that these products are preferred. Further, according to the present invention, it was found that at the time of performing the oligomerization reaction using the olefin, a total amount of polyolefin may be minimized due to a decrease in selectivity for the polyolefin capable of being formed as by-products except for 1-hexene and/or 1-octene, and a fouling phenomenon of the produced by-products on the inner wall of the reactor may be basically prevented.

In addition, the oligomerization reaction may be performed under slurry phase conditions, solution phase conditions, or the like.

The method of oligomerizing an olefin according to the exemplary embodiment of the present invention is performed at an arbitrary suitable temperature. Here, the suitable temperature may be 0 to 200° C., preferably, room temperature (20° C.) to 100° C., and more preferably 40 to 70° C.

In addition, a reaction solvent used under the solution phase conditions is not limited but may be selected from (C3-C20) hydrocarbon based solvent. A non-restrictive example of the hydrocarbon based solvent may be one or more selected from butane, pentane, hexane, heptane, octane, isooctane, nonane, decane, dodecane, cyclohexane, methylcyclohexane (MCH), methylcyclopentane (MCP), benzene, toluene, xylene, ethylbenzene, and the like, and preferably, one or more selected from hexane, heptane, cyclohexane, methylcyclohexane (MCH), methylcyclopentane (MCP), and the like.

Further, the method of oligomerizing an olefin according to the exemplary embodiment of the present invention is performed at a pressure of 1 bar (atmospheric pressure) to 500 bar, preferably atmospheric pressure to 100 bar, and more preferably atmospheric pressure to 60 bar.

According to the present invention, it was confirmed that as the predetermined hydrocarbon based compound, particularly, the petroleum based wax and/or the polyolefin wax having a melting point of 30 to 130° C. is used, an effect of decreasing the total amount of the polyolefins produced as the by-products may be significantly increased, and a phenomenon that the produced polyolefins are adhered onto the inner wall of the reactor may be effectively suppressed.

In the method of oligomerizing an olefin according to the exemplary embodiment of the present invention, in the catalyst composition for oligomerizing the olefin, the main catalyst and the cocatalyst may be preferably mixed in a molar ratio of 1:10 to 1:10000, but are not limited thereto.

According to an exemplary embodiment of the present invention, an alpha-olefin oligomer composition includes: petroleum based wax having a melting point of 30 to 130° C. and an alpha-olefin oligomer.

According to an exemplary embodiment of the present invention, an alpha-olefin oligomer composition includes: polyolefin wax having a melting point of 30 to 130° C. and an alpha-olefin oligomer.

As the alpha-olefin oligomer according to the exemplary embodiment of the present invention, 1-hexene, 1-octene, or a mixture thereof is preferred.

Here, a content of the petroleum based wax and/or the polyolefin wax in the alpha-olefin oligomer composition is not limited, but the petroleum based wax and/or the polyolefin wax may be contained in a content of 0.001 to 1000 ppm, and more preferably 0.001 to 500 ppm in the alpha-olefin oligomer composition.

The present invention will be understood more fully from the following Examples, and the following Examples are for illustrating the present invention and not for limiting the scope of the present invention. Further, unless otherwise described, the following Examples of the present invention were performed in a semi-batch reactor, and all organic solvents used in reactions were used after sufficiently removing moisture, oxygen, other catalyst poison materials, and the like, by allowing the organic solvents to pass through a tube filled with silica gel, molecular sieve 5 A, and activated alumina and to be bubbled by high-purity nitrogen. All reactions were carried out under a nitrogen atmosphere, and most of the reagents were purchased from Aldrich or STREM and used. As methylaluminoxane or modified aluminoxane (for example, mMAO-12, mMAO-3A, or mMAO-7), AkzoNobel products were purchased and used. A molecular weight of methylaluminoxane was calculated as 58.016 g/mol, and a molecular weight of modified aluminoxane (mMAO-3A) used in Examples was calculated as 70.07 g/mol. Amounts of reaction products obtained in the following Examples and Comparative Examples were analyzed by the following method.

[Analysis of contents (wt %) of 1-hexane and 1-octene in reaction products (LAO)]

Contents (wt %) of 1-hexene and 1-octene in a reaction solution were analyzed using Agilent GC7890.

Preparation Example 1

Preparation of bis-[(S,S)-(phenyl)$_2$PCH(methyl)CH(methyl)P(phenyl)$_2$ dichloro(μ-chloro)chromium] ([CrCl$_2$(μ-Cl){(P,P)-k2-(S,S)-((Ph)$_2$P(Me)CH—CH(Me)P(Ph)$_2$)}]$_2$)

After 1.1 g (3.0 mmol) of tris(tetrahydrofuran)chromium trichloride (CrCl$_3$(THF)$_3$) was dissolved in 100 mL of dichloromethane, 1.28 g (3.0 mmol) of (S,S)-(phenyl)$_2$PCH(methyl)CH(methyl)P(phenyl)$_2$ ligand compound was also dissolved in 50 mL of dichloromethane and slowly added thereto. After the reactants were stirred for 3 hours, volatile materials were removed therefrom under vacuum, and 100 mL of petroleum ether was added dropwise thereto, thereby obtaining a blue solid as a precipitate. The resultant was washed with 100 mL of petroleum ether two times, thereby obtaining 1.58 g of the title compound (yield: 90%).

Example 1

1 L of methylcyclohexane (MCH) was injected into a 2 L semi-batch reactor purged with nitrogen after being sufficiently dried, and 1 g of petroleum jelly (trade name: White Protopet®) was dispersed in 10 mL of MCH to thereby be injected into the semi-batch reactor. After injecting 1.57 g (4 mmol) of 18 wt % mMAO-3A heptane solution (cocatalyst) into the reactor, a temperature of the semi-batch reactor was heated to 60° C. Then, pressure in the reactor was raised to 27 bar using ethylene. After injecting 3.1 mg (5.3 μmol-Cr) of bis-[(S,S)-(phenyl)$_2$PCH(methyl)CH(methyl)P(phenyl)$_2$ dichloro(μ-chloro)chromium] into an upper catalyst port of the semi-batch reactor, the pressure in the reactor was raised to 30 bar using ethylene. Then, ethylene was continuously supplied, thereby performing an oligomerization reaction for 80 minutes (stirring condition: 200 rpm). Thereafter, in order to inactive a catalyst, 100 ml of 10 vol % hydrochloric acid aqueous solution-containing ethanol (wt:wt, 10 vol % hydrochloric acid aqueous solution:ethanol=1:1) was injected into the reaction solution to terminate the reaction, and then, a reaction product was filtered and separated. A reaction product recovered from a reaction filtrate was dried in a vacuum oven at 60° C. for 8 hours.

A weight of a primary polymer (floating polyethylene $1^{st}$ PE) recovered by the filtration was measured. Further, after 1 L of MCH was injected into the semi-batch reactor from which the reaction product was removed and stirred at 150° C. for 1 hour, a reaction solution was drained, such that a weight of a secondary polymer (adherent polyethylene, $2^{nd}$ PE) was measured. Further, an image obtained by photographing an inner side of the reactor after the reaction is illustrated in FIG. 1.

As a result, 429 g of the reaction product (LAO, C6+C8) was obtained, and among them, an amount of 1-hexene was 202 g, and an amount of 1-octene was 227 g. Further, a total amount of polyethylenes (PE) obtained as by-products was 0.57 g, and among them, an amount of the primary polymer was 0.37 g and an amount of the secondary polymer was 0.2 g (see the following Table 1).

Example 2

A reaction product was obtained in the same manner as in Example 1 except for using 5.8 mg (10.0 µmol-Cr) of bis-[(S,S)-(phenyl)$_2$PCH(methyl)CH(methyl)P(phenyl)$_2$ dichloro(µ-chloro)chromium], and weights of primary and secondary polymers were measured by the same method as in Example 1.

As a result, 588 g of the reaction product (LAO, C6+C8) was obtained, and among them, an amount of 1-hexene was 247 g, and an amount of 1-octene was 341 g. Further, a total amount of polyethylenes (PE) obtained as by-products was 2.12 g, and among them, an amount of the primary polymer was 1.24 g and an amount of the secondary polymer was 0.88 g (see the following Table 1).

Example 3

A reaction product was obtained in the same manner as in Example 1 except for using 1.0 g of Mitsui Hi-wax 220P (melting point: 110° C., Mitsui Chemicals Inc.) instead of 1 g of petroleum jelly (trade name: White Protopet®), and weights of primary and secondary polymers were measured by the same method as in Example 1.

As a result, 472 g of the reaction product (LAO, C6+C8) was obtained, and among them, an amount of 1-hexene was 208 g, and an amount of 1-octene was 264 g. Further, a total amount of polyethylenes (PE) obtained as by-products was 0.11 g, and among them, an amount of the primary polymer was 0.10 g and an amount of the secondary polymer was 0.01 g (see the following Table 1).

Example 4

A reaction product was obtained in the same manner as in Example 1 except for using 1 g of Mitsui Hi-wax 400P (melting point: 126° C., Mitsui Chemicals Inc.) instead of 1 g of petroleum jelly (trade name: White Protopet®), and weights of primary and secondary polymers were measured by the same method as in Comparative Example 3.

As a result, 458 g of the reaction product (LAO, C6+C8) was obtained, and among them, an amount of 1-hexene was 185 g, and an amount of 1-octene was 273 g. Further, a total amount of polyethylenes (PE) obtained as by-products was 0.34 g, and among them, an amount of the primary polymer was 0.21 g and an amount of the secondary polymer was 0.13 g (see the following Table 1).

Example 5

A reaction product was obtained in the same manner as in Example 1 except for using 1 g of Mitsui Hi-wax 720P (melting point: 113° C., Mitsui Chemicals Inc.) instead of 1 g of petroleum jelly (trade name: White Protopet®), and weights of primary and secondary polymers were measured by the same method as in Comparative Example 3.

As a result, 470 g of the reaction product (LAO, C6+C8) was obtained, and among them, an amount of 1-hexene was 188 g, and an amount of 1-octene was 282 g. Further, a total amount of polyethylenes (PE) obtained as by-products was 0.83 g, and among them, an amount of the primary polymer was 0.72 g and an amount of the secondary polymer was 0.11 g (see the following Table 1).

Example 6

A reaction product was obtained in the same manner as in Example 1 except for using 0.5 g of petroleum jelly (trade name: White Protopet®) instead of 1 g of petroleum jelly (trade name: White Protopet®) and using 2.32 g (4 mmol) of 10 wt % MAO toluene solution instead of 18 wt % mMAO-3A heptane solution (cocatalyst), and weights of primary and secondary polymers were measured by the same method as in Example 1.

As a result, 386 g of the reaction product (LAO, C6+C8) was obtained, and among them, an amount of 1-hexene was 117 g, and an amount of 1-octene was 269 g. Further, a total amount of polyethylenes (PE) obtained as by-products was 0.72 g, and among them, an amount of the primary polymer was 0.06 g and an amount of the secondary polymer was 0.66 g (see the following Table 1).

Example 7

A reaction product was obtained in the same manner as in Example 1 except for using 2.32 g (4 mmol) of 10 wt % MAO toluene solution instead of 18 wt % mMAO-3A heptane solution (cocatalyst), and weights of primary and secondary polymers were measured by the same method as in Example 1.

As a result, 416 g of the reaction product (LAO, C6+C8) was obtained, and among them, an amount of 1-hexene was 126 g, and an amount of 1-octene was 290 g. Further, a total amount of polyethylenes (PE) obtained as by-products was 0.75 g, and among them, an amount of the primary polymer was 0.14 g and an amount of the secondary polymer was 0.61 g (see the following Table 1).

Example 8

A reaction product was obtained in the same manner as in Example 1 except for using 3 g of petroleum jelly (trade name: White Protopet®) instead of 1 g of petroleum jelly (trade name: White Protopet®) and using 2.32 g (4 mmol) of 10 wt % MAO toluene solution instead of 18 wt % mMAO-3A heptane solution (cocatalyst), and weights of primary and secondary polymers were measured by the same method as in Example 1.

As a result, 428 g of the reaction product (LAO, C6+C8) was obtained, and among them, an amount of 1-hexene was 129 g, and an amount of 1-octene was 299 g. Further, a total amount of polyethylenes (PE) obtained as by-products was 0.68 g, and among them, an amount of the primary polymer was 0.13 g and an amount of the secondary polymer was 0.55 g (see the following Table 1).

Example 9

A reaction product was obtained in the same manner as in Example 2 except for using 0.5 g of paraffin wax instead of 1 g of petroleum jelly (trade name: White Protopet®), and weights of primary and secondary polymers were measured by the same method as in Example 1.

As a result, 608 g of the reaction product (LAO, C6+C8) was obtained, and among them, an amount of 1-hexene was 235 g, and an amount of 1-octene was 373 g. Further, a total amount of polyethylenes (PE) obtained as by-products was 1.71 g, and among them, an amount of the primary polymer was 0.48 g and an amount of the secondary polymer was 1.23 g (see the following Table 1).

Comparative Example 1

A reaction product was obtained in the same manner as in Example 1 except for not using petroleum jelly (trade name: White Protopet®), and weights of primary and secondary polymers were measured by the same method as in Example 1. Further, an image obtained by photographing an inner side of the reactor after the reaction is illustrated in FIG. 2.

As a result, 411 g of the reaction product (LAO, C6+C8) was obtained, and among them, an amount of 1-hexene was 176 g, and an amount of 1-octene was 235 g. Further, a total amount of polyethylenes (PE) obtained as by-products was 1.17 g, and among them, an amount of the primary polymer was 0.47 g and an amount of the secondary polymer was 0.70 g (see the following Table 1).

Comparative Example 2

A reaction product was obtained in the same manner as in Comparative Example 1 except for using 5.8 mg (10.0 μmol-Cr) of bis-[(S,S)-(phenyl)$_2$PCH(methyl)CH(methyl)P(phenyl)$_2$dichloro(μ-chloro)chromium], and weights of primary and secondary polymers were measured by the same method as in Example 1.

As a result, 494 g of the reaction product (LAO, C6+C8) was obtained, and among them, an amount of 1-hexene was 226 g, and an amount of 1-octene was 268 g. Further, a total amount of polyethylenes (PE) obtained as by-products was 2.84 g, and among them, an amount of the primary polymer was 2.3 g and an amount of the secondary polymer was 0.54 g (see the following Table 1).

Comparative Example 3

A reaction product was obtained in the same manner as in Comparative Example 1 except for using 2.32 g (4 mmol) of 10 wt % MAO toluene solution instead of 18 wt % mMAO-3A heptane solution (cocatalyst), and weights of primary and secondary polymers were measured by the same method as in Example 1. Further, an image obtained by photographing an inner side of the reactor after the reaction is illustrated in FIG. 3.

As a result, 419 g of the reaction product (LAO, C6+C8) was obtained, and among them, an amount of 1-hexene was 128 g, and an amount of 1-octene was 290 g. Further, a total amount of polyethylenes (PE) obtained as by-products was 0.98 g, and among them, an amount of the primary polymer was 0.22 g and an amount of the secondary polymer was 0.76 g (see the following Table 1).

Comparative Example 4

A reaction product was obtained in the same manner as in Example 1 except for using 1 g of mineral oil (Sigma Aldrich) instead of 1 g of petroleum jelly (trade name: White Protopet®), and weights of primary and secondary polymers were measured by the same method as in Example 1.

As a result, 431 g of the reaction product (LAO, C6+C8) was obtained, and among them, an amount of 1-hexene was 207 g, and an amount of 1-octene was 224 g. Further, a total amount of polyethylenes (PE) obtained as by-products was 1.2 g, and among them, an amount of the primary polymer was 0.83 g and an amount of the secondary polymer was 0.37 g (see the following Table 1).

Comparative Example 5

A reaction product was obtained in the same manner as in Example 2 except for using 1 g of paraffin oil (Sigma Aldrich) instead of 1 g of petroleum jelly (trade name: White Protopet®), and weights of primary and secondary polymers were measured by the same method as in Example 1.

As a result, 597 g of the reaction product (LAO, C6+C8) was obtained, and among them, an amount of 1-hexene was 227 g, and an amount of 1-octene was 370 g. Further, a total amount of polyethylenes (PE) obtained as by-products was 3.12 g, and among them, an amount of the primary polymer was 1.34 g and an amount of the secondary polymer was 1.78 g (see the following Table 1).

Comparative Example 6

A reaction product was obtained in the same manner as in Example 1 except for using 1 g of YUBASE 3 (SK Energy Co., Ltd.) instead of 1 g of petroleum jelly (trade name: White Protopet®), and weights of primary and secondary polymers were measured by the same method as in Example 1.

As a result, 442 g of the reaction product (LAO, C6+C8) was obtained, and among them, an amount of 1-hexene was 185 g, and an amount of 1-octene was 257 g. Further, a total amount of polyethylenes (PE) obtained as by-products was 1.28 g, and among them, an amount of the primary polymer was 0.86 g and an amount of the secondary polymer was 0.42 g (see the following Table 1).

Comparative Example 7

A reaction product was obtained in the same manner as in Example 2 except for using 1 g of YUBASE 6 (SK Energy Co., Ltd.) instead of 1 g of petroleum jelly (trade name: White Protopet®), and weights of primary and secondary polymers were measured by the same method as in Example 1.

As a result, 426 g of the reaction product (LAO, C6+C8) was obtained, and among them, an amount of 1-hexene was 181 g, and an amount of 1-octene was 245 g. Further, a total amount of polyethylenes (PE) obtained as by-products was 1.33 g, and among them, an amount of the primary polymer was 0.76 g and an amount of the secondary polymer was 0.57 g (see the following Table 1).

Comparative Example 8

A reaction product was obtained in the same manner as in Example 2 except for using 0.05 g of polypropylene glycol (Sigma Aldrich) instead of 1 g of petroleum jelly (trade name: White Protopet®), and weights of primary and secondary polymers were measured by the same method as in Example 1.

As a result, 13 g of the reaction product (LAO, C6+C8) was obtained, and among them, an amount of 1-hexene was 4 g, and an amount of 1-octene was 9 g. Further, a total amount of polyethylenes (PE) obtained as by-products was 2.78 g, and among them, an amount of the primary polymer was 0.42 g and an amount of the secondary polymer was 2.36 g (see the following Table 1).

TABLE 1

| | Fouling Inhibitor | | Production | | | |
|---|---|---|---|---|---|---|
| Example | Kind | Use Amount (g) | Amount of LAO (g, C6 + C8) | Total PE g | Total PE Wt % | Molecular Weight of Fouling Inhibitor (Phase) |
| 1 | petroleumjelly | 1.0 | 429 | 0.57 | 0.13 | 350-650 (semi-solid) |
| 3 | Hi-wax 220P | 1.0 | 472 | 0.11 | 0.02 | 2,000 (solid) |
| 4 | Hi-wax 400P | 1.0 | 458 | 0.34 | 0.07 | 4,000 (solid) |
| 5 | Hi-wax 720P | 1.0 | 470 | 0.83 | 0.18 | 7,000 (solid) |
| 6 | petroleumjelly | 0.5 | 386 | 0.72 | 0.19 | 350-650 (semi-solid) |
| 7 | petroleumjelly | 1.0 | 416 | 0.75 | 0.18 | 350-650 (semi-solid) |
| 8 | petroleumjelly | 3.0 | 428 | 0.68 | 0.16 | 350-650 (semi-solid) |
| Comparative Example 1 | — | — | 411 | 1.17 | 0.28 | — |
| Comparative Example 2 | — | — | 494 | 2.84 | 0.57 | — |
| Comparative Example 3 | — | — | 419 | 0.98 | 0.23 | — |
| Comparative Example 4 | Mineral oil | 1.0 | 431 | 1.20 | 0.28 | 300-450 (oil) |
| Comparative Example 5 | Paraffin oil | 1.0 | 597 | 3.12 | 0.52 | 300-450 (oil) |
| Comparative Example 6 | YUBASE3 | 1.0 | 442 | 1.28 | 0.29 | 300-400 (oil) |
| Comparative Example 7 | YUBASE6 | 1.0 | 426 | 1.33 | 0.31 | 500 (oil) |
| Comparative Example 8 | Polypropylene glycol | 0.05 | 13 | 2.78 | 17.89 | 2000 (oil) |

As illustrated in Table 1, according to the present invention, it was confirmed that 1-hexene and 1-octene may be produced with a high yield under mild conditions, and a total amount of polyethylene (PE) produced as by-products may be effectively decreased, and at the same time, an amount of polyethylene adhered into the reactor may be significantly decreased.

More specifically, it may be confirmed that in Example 1 according to the present invention, the total amount of polyethylene (PE) may be significantly decreased to about 46.74% of that in Comparative Example 1 in which the fouling inhibitor was not used, and the amount of adherent polyethylene may be decreased to about 28.57%.

This effect was not recognized in the related art, and there was no specific application example thereof.

Although the exemplary embodiments of the present invention have been disclosed in detail, those skilled in the art will appreciate that various modifications are possible, without departing from the scope and spirit of the invention as disclosed in the accompanying claims. Therefore, modifications of exemplary embodiments of the present invention will also be included in the scope of the present invention.

The invention claimed is:

1. A method of oligomerizing an olefin, the method comprising: injecting a fouling inhibitor comprising a petroleum based wax into a reactor; injecting a catalyst composition into the reactor; and injecting the olefin into the reactor to perform an oligomerization reaction,
    wherein the petroleum based wax is semi-solid or solid,
    wherein the molecular weight of the petroleum based wax is 350 to 1000, and
    wherein the petroleum based wax is one or more selected from petroleum jelly, paraffin wax, and microcrystalline wax.

2. The method of claim 1, wherein the petroleum based wax has a hetero atom ratio of 0.0001 to 0.01 in each molecule.

3. The method of claim 1, wherein the petroleum based wax is contained in a range of 0.05 to 10 wt % based on a total weight of a medium in the reactor.

4. The method of claim 1, wherein the catalyst composition contains a main catalyst and a cocatalyst,
    the main catalyst being a complex in which a transition metal and a hetero atom ligand represented by the following Chemical Formula 1 are coordinated with each other,
    [Chemical Formula 1]
    $(R^1)_n A\text{-}B\text{-}C(R^2)_m$,
    wherein in Chemical Formula 1,
    A and C are each independently selected from the group consisting of phosphorus, arsenic, antimony, oxygen, bismuth, sulfur, selenium, and nitrogen,
    B is a linking group between A and C,
    n and m are each independently integers determined by valences and an oxidation states of A and C, respectively, and
    $R^1$ and $R^2$ are each independently selected from the group consisting of substituted or unsubstituted hydrocarbyl and substituted or unsubstituted heterohydrocarbyl, $R^1$(s) are equal to or different from each other when n≥2, and $R^2$(s) are equal to or different from each other when m≥2.

5. The method of claim 4, wherein B is selected from an organic linking group including substituted or unsubstituted hydrocarbylene and substituted or unsubstituted heterohydrocarbylene; and an inorganic linking group including a single atom link.

6. The method of claim 4, wherein the hetero atom ligand is represented by the following Chemical Formula 2,

[Chemical Formula 2]

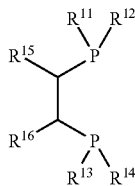

wherein in Chemical Formula 2, $R^{11}$ to $R^{14}$ are each independently selected from the group consisting of substituted or unsubstituted hydrocarbyl and substituted or unsubstituted heterohydrocarbyl, and $R^{15}$ and $R^{16}$ are each independently substituted or unsubstituted hydrocarbyl, or are linked with each other by substituted or unsubstituted hydrocarbylene or substituted or unsubstituted heterohydrocarbylene to form a ring.

7. The method of claim 4, wherein the cocatalyst is one or more selected from an organic aluminum compound and an organic boron compound.

8. The method of claim 1, wherein the performing the oligomerization reaction is performed in a temperature range of 0 to 200° C.

9. The method of claim 1, wherein the performing the oligomerization reaction is performed in a temperature range of 40 to 100° C.

10. The method of claim 1, wherein the performing the oligomerization reaction is performed in a pressure range of 1 to 800 bar.

11. The method of claim 1, wherein the olefin is ethylene, and 1-hexene, 1-octene, or a mixture thereof is selectively prepared.

* * * * *